(12) United States Patent
Chen et al.

(10) Patent No.: US 9,958,444 B2
(45) Date of Patent: May 1, 2018

(54) APPARATUS, SYSTEMS AND METHODS FOR SENSING AN ANALYTE SUCH AS ETHANOL

(71) Applicants: Scott W. T. Chen, Waterloo (CA);
John T. Carroll, Waterloo (CA);
Raafat R. Mansour, Waterloo (CA)

(72) Inventors: Scott W. T. Chen, Waterloo (CA);
John T. Carroll, Waterloo (CA);
Raafat R. Mansour, Waterloo (CA)

(73) Assignee: Sober stearing Sensors Canada, Inc., Kitchener, Ontario (CA)

( * ) Notice: Subject to any disclaimer, the term of this patent is extended or adjusted under 35 U.S.C. 154(b) by 287 days.

(21) Appl. No.: 14/292,740

(22) Filed: May 30, 2014

(65) Prior Publication Data

US 2015/0346197 A1 Dec. 3, 2015

(51) Int. Cl.
*G01N 33/545* (2006.01)
*A61B 5/145* (2006.01)
*G01N 33/483* (2006.01)
*A61B 5/1477* (2006.01)
*A61B 5/00* (2006.01)

(52) U.S. Cl.
CPC ......... *G01N 33/545* (2013.01); *A61B 5/1477* (2013.01); *A61B 5/14546* (2013.01); *A61B 5/4845* (2013.01); *G01N 33/4836* (2013.01); *A61B 5/681* (2013.01); *A61B 5/6893* (2013.01); *A61B 2562/028* (2013.01); *A61B 2562/06* (2013.01)

(58) Field of Classification Search
CPC .. G01N 33/53; G01N 33/4836; A61B 5/4845; A61B 5/1477; A61B 5/14546; A61B 2562/06; A61B 2562/028; A61B 5/6893; A61B 5/681; A61B 5/0492; A61B 2562/247; G06F 3/015
See application file for complete search history.

(56) References Cited

U.S. PATENT DOCUMENTS

| | | | | |
|---|---|---|---|---|
| 4,571,543 | A * | 2/1986 | Raymond | G01N 27/227 257/414 |
| 5,491,097 | A * | 2/1996 | Ribi | G01N 33/5438 422/82.01 |
| 6,400,974 | B1 * | 6/2002 | Lesho | A61B 5/0031 600/345 |
| 6,477,479 | B1 * | 11/2002 | Mansky | B01J 19/0046 422/68.1 |
| 7,922,975 | B2 * | 4/2011 | Subramanyam | G01N 27/221 422/82.01 |

(Continued)

*Primary Examiner* — Lore R Jarrett
(74) *Attorney, Agent, or Firm* — Bereskin & Parr

(57) ABSTRACT

According to one aspect, a system for sensing ethanol from human skin, that comprises at least one apparatus for sensing ethanol and a coupling matrix readout extraction unit for performing a method of extracting a coupling-matrix readout. The at least one sensing apparatus and the coupling matrix readout extraction may be mounted on a substrate. The substrate may be adapted such that it can be formed into a wearable accessory that can be worn by a human subject. When the wearable accessory is worn by the human subject such that the subject provides a skin tissue sample to the accessory, the presence or concentration of ethanol and other compounds may be determined from the vapor associated with the tissue sample.

10 Claims, 12 Drawing Sheets

(56) References Cited

U.S. PATENT DOCUMENTS

| | | | | |
|---|---|---|---|---|
| 8,246,910 | B2* | 8/2012 | Dhirani | G01N 30/64 422/50 |
| 2002/0137998 | A1* | 9/2002 | Smart | A61B 5/14532 600/347 |
| 2005/0153425 | A1* | 7/2005 | Xu | C12M 25/08 435/287.1 |
| 2006/0160244 | A1* | 7/2006 | Sawa | A61B 5/14514 436/177 |
| 2009/0296307 | A1* | 12/2009 | Siamak | B81C 1/00246 361/281 |
| 2010/0055666 | A1* | 3/2010 | Wimberger-Friedl | G01N 21/6454 435/4 |
| 2011/0031983 | A1* | 2/2011 | David | G01N 27/125 324/663 |
| 2011/0160554 | A1* | 6/2011 | Megej | A61B 5/0507 600/365 |
| 2015/0141784 | A1* | 5/2015 | Morun | G06F 3/015 600/372 |

* cited by examiner

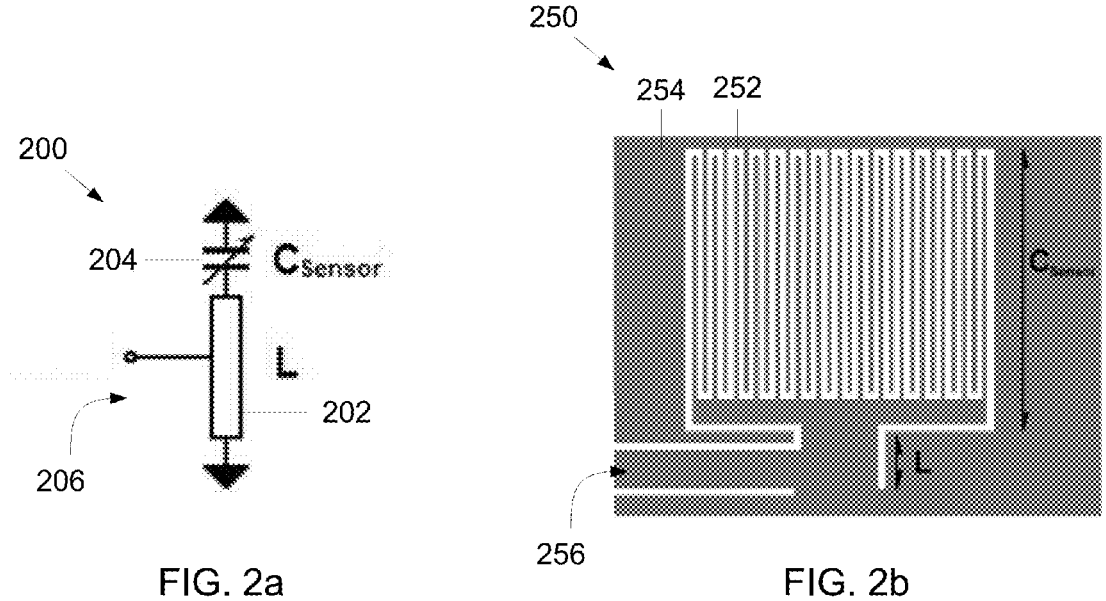
FIG. 2a
FIG. 2b
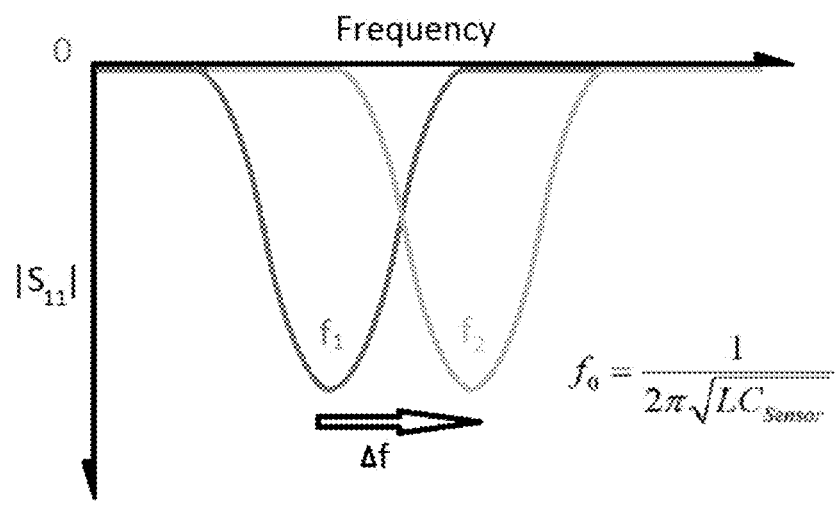
FIG. 2c

700

750

Measured and Model-Mapped Sensor Response on 5000ppm Ethanol

Measured and Model-Mapped Sensor Response on 5000ppm Acetone

APPARATUS, SYSTEMS AND METHODS FOR SENSING AN ANALYTE SUCH AS ETHANOL

TECHNICAL FIELD

The embodiments disclosed herein relate to apparatus, systems and methods for sensing an analyte, and more specifically to a rigid or flexible epidermal sensor array using a coupling matrix analysis technique for sensing an analyte such as ethanol.

INTRODUCTION

The following paragraphs are not an admission that anything discussed therein is prior art or part of the knowledge of persons skilled in the art.

Resonant sensors may be used for improved sensitivity levels at a mechanical or electrical resonant frequency at which the sensor output characteristics are amplified with respect to corresponding ambient stimulations.

Resonant sensor platforms have been proposed in U.S. Pat. No. 5,942,991 to Gaudreau et al., and U.S. Pat. No. 7,922,975 to Subramanyam. These publications outline the output characteristics of a resonant sensor operating at radio frequencies for both wired and wireless applications The responses of a resonant sensor can be obtained either by transmission response or reflection response. In both cases, the sensor is excited with electrical signals within a selected set of frequencies, and the readout is measured by the ratio between the supplied power and the returned power, where the former serves as the reference and the latter changes with the sensor response against the target environmental parameter.

Common sensor arrays, as well as resonant sensor arrays, are constructed with individual sensors sampled either serially through a single readout unit, or in parallel with dedicated readout unit for every sensor. A serial configuration may reduce the footprint of the readout circuit, whereas a parallel configuration may allow for readout speed to be maximized. However, mutual electrical separation among the sensors is mandatory to minimize the inter-sensor interference. This separation may limit the achievable design size.

Implementation of sensors and sensor arrays on flexible materials may lead to new applications that implement foldable and contour-conformal sensor devices. However, sensors on flexible materials are prone to compromised performance due to material deformation. This unwanted physical sensor interference may be amplified near sensor resonance.

SUMMARY

According to some embodiments, there are apparatus, methods, and systems for sensing ethanol from human skin.

The system may comprise an apparatus, which may include a sensor array, and which can be mounted to a substrate material. Additionally, the apparatus may be connected to a coupling matrix readout extraction unit, so that a method for extracting a coupling matrix readout can be performed.

In some embodiments, the substrate may comprise a flexible material selected or designed so that it can be shaped or form-fitted around a vehicle, such as on or around a part of the vehicle that is likely to be in contact with a human user. For example, the flexible substrate, and therefore, the apparatus or system, may be wrapped on a steering wheel. In such a configuration, a driver using the steering wheel may grasp the steering wheel, and thereby present a tissue sample to the sensor array.

According to other embodiments, the flexible material may be selected or designed so that it can be shaped into a wearable system or accessory. For example, the wearable system may be a bracelet or other device in contact with the wearer's skin, which can be worn by a user who provides a tissue sample to the sensor array when the bracelet is worn.

In other cases, the substrate may comprise a rigid material, such as in a case when a flexible material is not required. For example, the rigid material may be selected or designed so that it can be shaped into a wearable system or accessory. For example, the wearable system may be a wrist-watch-type device in contact with the wearer's skin.

According to some embodiments, there is an apparatus for sensing an analyte. The apparatus may be constructed in layers, using a substrate layer, a conductive layer, and a frame layer, as well as other layers.

The substrate may have a rigid region, corresponding to a relatively thick section of the substrate layer. This rigid region may support a sensor block.

The sensor block may have frame members that extend upwards from the substrate to define a pocket. For example, the frame members may be formed as walls, surrounding and enclosing the pocket, which may remain open at the top. The top ends of the frame members may be formed so that they can withstand contact with a tissue sample, such as human skin or tissue from another animal. In some cases, the tissue sample is the area of skin of a subject person to which the sensor block is exposed.

Part or all of a sensor may be located at the bottom of the pocket, or at least at a distance from the first end. As such, the sensor may be protected from contact with a tissue sample by the frame members.

According to some embodiments, the sensor may be an electrical resonant sensor, such as may be implemented as a coplanar waveguide structure for use at microwave frequencies.

The sensor may include a substance with properties reactive to ambient conditions. For example, the substance may be an analyte-reactive substance, such that the electrical properties of the substance vary in the presence of a particular analyte. According to some such embodiments, the substance may be a chemi-absorbent polymer.

The substance, such as an analyte-reactive substance or chemi-absorbent polymer, may be placed at the bottom of the pocket so that it covers at least part of the sensor structure. For example, if the substance is a chemi-absorbent polymer, and the sensor structure is a coplanar waveguide, the chemi-absorbent polymer may be placed at the bottom of the pocket so that it covers a capacitive region of the coplanar waveguide sensor.

According to some embodiments, the apparatus may be formed with a second sensor block coupled to the first sensor block. In some cases, the second sensor block may be coupled to the first sensor block on a rigid substrate, while in other cases, the second sensor block may be coupled to the first sensor block with a flexible node.

Any number of sensor blocks may be coupled together using any combination of rigid and/or flexible nodes. In some embodiments, multiple sensor blocks may be coupled together in order to form a sensor array.

The flexible node may comprise a thinner layer of the substrate than the substrate layer supporting the sensor block. As such, the substrate may be seen as having a rigid-flex configuration, or as operating as a living hinge.

According to some other embodiments, there is a method for extracting a coupling matrix readout from a sensor array. The method may include exciting a sensor array with an excitation signal, and then reading the reflection of the signal from the sensor port. A coupling matrix analysis technique may then be used in order to decouple the sensor reading, and obtain a reading that is free from inter-sensor interference.

In some embodiments, the coupling matrix analysis technique may utilize one or more resonant parameters obtained from the reflection signal. For example, in some embodiments, the resonant parameters may include the sensor capacitance, the sensor inductance, and the inter-sensor interference.

Once the resonant parameters have been obtained, they may be compared to known resonant parameters in order to determine ambient conditions, such as the presence of an analyte.

Other aspects and features will become apparent to those ordinarily skilled in the art upon review of the following description of some exemplary embodiments as described herein.

BRIEF DESCRIPTION OF THE DRAWINGS

The drawings included herewith are for illustrating various examples of articles, methods, and apparatuses of the present specification. In the drawings:

FIG. 2a is a circuit diagram of a single-port inductor-capacitor resonant circuit;

FIG. 2b is a plan view of a single-port coplanar waveguide resonant circuit;

FIG. 2c is a reflection response curve of a single-port, single-resonator sensor as taken at the input port;

DETAILED DESCRIPTION OF SOME EMBODIMENTS

Various apparatus or processes will be described below to provide an example of an embodiment of each claimed embodiment. No embodiment described below limits any claimed embodiment and any claimed embodiment may cover processes or apparatus that differ from those described below. The claimed embodiments are not limited to apparatus or processes having all of the features of any one apparatus or process described below or to features common to multiple or all of the apparatus described below. It is possible that an apparatus or process described below is not an embodiment of any claimed embodiment. Any embodiment disclosed below that is not claimed in this document may be the subject matter of another protective instrument, for example, a continuing patent application, and the applicants, inventors or owners do not intend to abandon, disclaim or dedicate to the public any such embodiment by its disclosure in this document.

Figure 1:
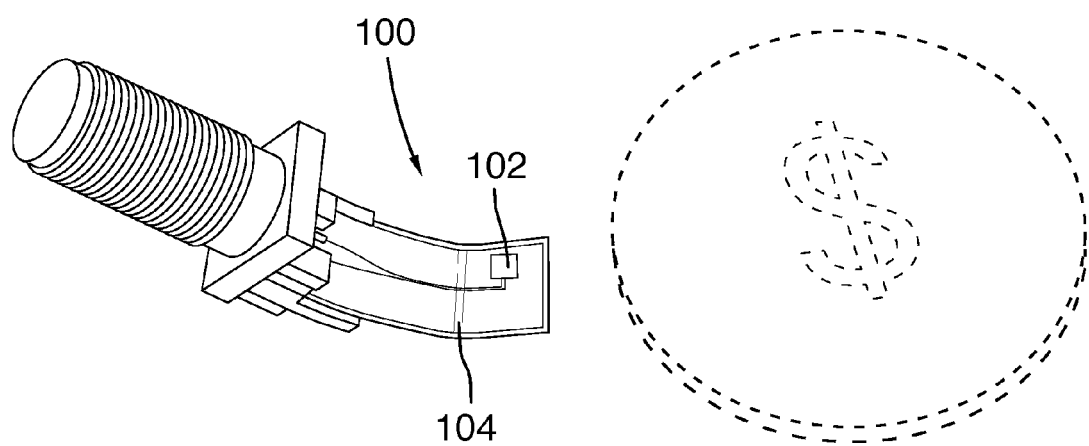
FIG. 1 is an image of a prototype single-port, two-sensor array according to one embodiment.

Referring now to FIG. 1, illustrated therein is a flexible resonant sensor array 100 according to one embodiment, and which includes a sensor 102 and a flexible node 104. Multiple sensors may be are arranged adjacent one another, so as to form a sensor array.

According to some embodiments, the sensor 102 and/or second sensor may be implemented using a resonator structure. A simple resonator can be modelled using an inductor and a capacitor, as shown in FIG. 2a.

FIG. 2a shows an example resonator structure 200 consisting of an inductor 202 and a capacitor 204, with an associated port 206.

A resonator structure may be implemented using a coplanar waveguide configuration. An example of a coplanar waveguide resonator 250 is shown in FIG. 2b. In this implementation, the coplanar waveguide resonator 250 consists of a trace 252 or a conductive layer such as copper, placed on a substrate 254. The particular geometry of the trace 252 determines a capacitance (e.g. $C_{Sensor}$) and an inductance (e.g. L) as seen by a port 256.

A resonator, for example, the resonator 200 or the resonator 250, can be used as a resonant sensor when either the capacitance (e.g. $C_{Sensor}$) or the inductance e.g. L), or both, are sensitive to at least one environmental condition.

Referring to FIG. 2c, there is shown a reflection curve of a single-port, single-resonator, such as the resonators 200 or 250. This curve shows the frequency response of the reflection, as given by the magnitude of $S_{11}$. The resonant or center frequency $f_0$ is provided by the expression:

$$f_0 = \frac{1}{2\pi\sqrt{LC_{Sensor}}}.$$

As shown in FIG. 2c, a first center frequency, $f_1$, may correspond to a first value of $C_{Sensor}$, and a second center frequency, $f_2$, may correspond to a second value of $C_{Sensor}$. The value of $C_{Sensor}$ may change, for example, when the capacitive structure of the resonator includes a substance whose electrical properties change, for example, in the presence of an ambient condition. Thus, $f_1$ may be the center frequency of the resonator when under a first ambient condition, and $f_2$ may be the center frequency of the resonator under a second ambient condition. The change in the center frequency is $\Delta f = f_2 - f_1$.

In order to achieve a flexible sensor array structure, a coplanar waveguide structure may be implemented using a flexible substrate material. For example, a commercially available rigid-flex substrate, such as a substrate using a Kapton® polyimide layer may be used.

Figure 3A:
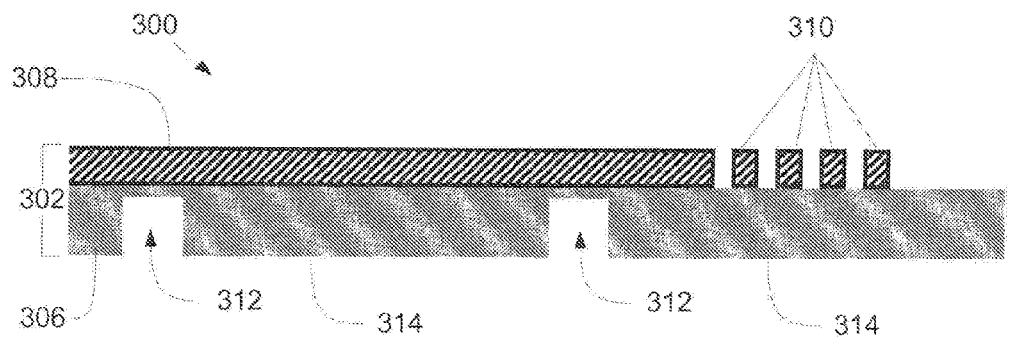
FIG. 3a is an elevation view of a sensor on a flexible substrate structure.

Referring to FIG. 3a, there is shown an example of coplanar waveguide structure 300 implemented on a rigid-flex structure 302. The rigid-flex structure 302 may be composed of a rigid-flex substrate 306 and a conductive layer 308, such as gold, copper, or any other conductive material.

In order to achieve flexibility, the substrate 306 is formed such that different regions have different thicknesses. For example, the substrate 306 may have at least one trench region 312, and at least one island region 314. Each trench region 312 is generally defined by a thinner layer of the substrate 306 as compared to the island regions 314.

A sensor 310 may be fabricated on a rigid island 314 of the substrate 306. For example, the sensor 310 may take a similar form as shown by the resonator 250 in FIG. 2b.

As the substrate 306 is flexed, the thin trenches 312 along the substrate 306 experience most of the flexed deformation, leaving the rigid islands 314 substantially undeformed, consequently protecting the sensor 310 from physical deformation.

According to some embodiments, the flexible trenches 312 may be formed by notches, or recesses in the substrate 306. The cross-section of the flexible trenches 312 may of various geometries, and may define rectangular notches, triangular wedges, curved channels, etc. In essence, the flexible trenches 312, in combination with the rigid islands 314, cooperate such that the rigid-flex substrate 302 can operate as a living hinge.

Figure 3B:
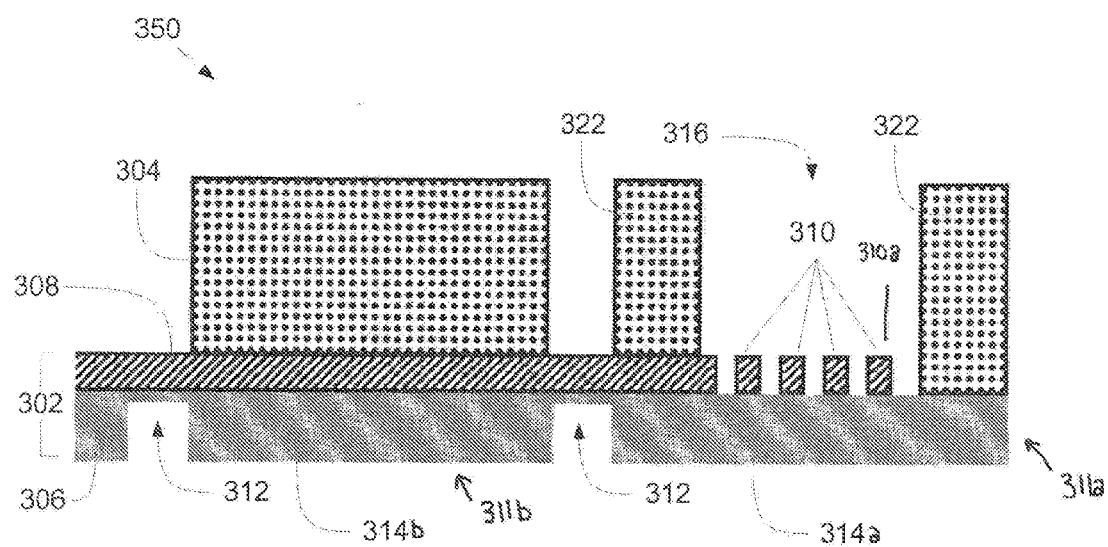
FIG. 3b is an elevation view of a sensor on a flexible substrate structure, having a structural frame forming a series of frames according to another embodiment.

Referring to FIG. 3b, there is shown an example of a frame-flex coplanar waveguide structure 350 comprising a rigid-flex structure 302 and an additional structural frame layer 304. The rigid-flex structure 302 may be composed of a rigid-flex substrate 306 and a conductive layer 308, such as gold, copper, or any other conductive material.

The structural frame layer 304 may be added on top of the rigid-flex layer 302. According to some embodiments, the structural frame layer 304 may be patterned with the same trench pattern as the substrate 306, thereby supplementing the rigidity of the rigid islands 314a and 314b and forming sensor blocks 311a and 311b thereupon, respectively. Additionally, an opening may be provided that exposes the capacitor portion 310a of the sensor 310. This opening, or absence of structural frame layer 304, results in a pocket 316. According to some embodiments, the pocket 316 may be a polymer pocket, which can contain a chemi-absorbent polymer or other analyte-reactive substance.

According to some embodiments, the provision of a polymer pocket, such as pocket 316, may allow for a repeatable polymer deposition within the pocket. Furthermore, the provision of a polymer pocket, such as pocket 316, may provide sufficient margin to prevent contact between the sensor 310 and a target sampling surface.

The pocket 316 may also allow for polymer deposition of a liquid polymer, by containing the liquid polymer within the pocket 316, and then subjecting the liquid polymer to conditions required to cure the polymer. For example, the liquid polymer deposited within the pocket 316 may be a chemi-absorbent polymer.

Figure 4:
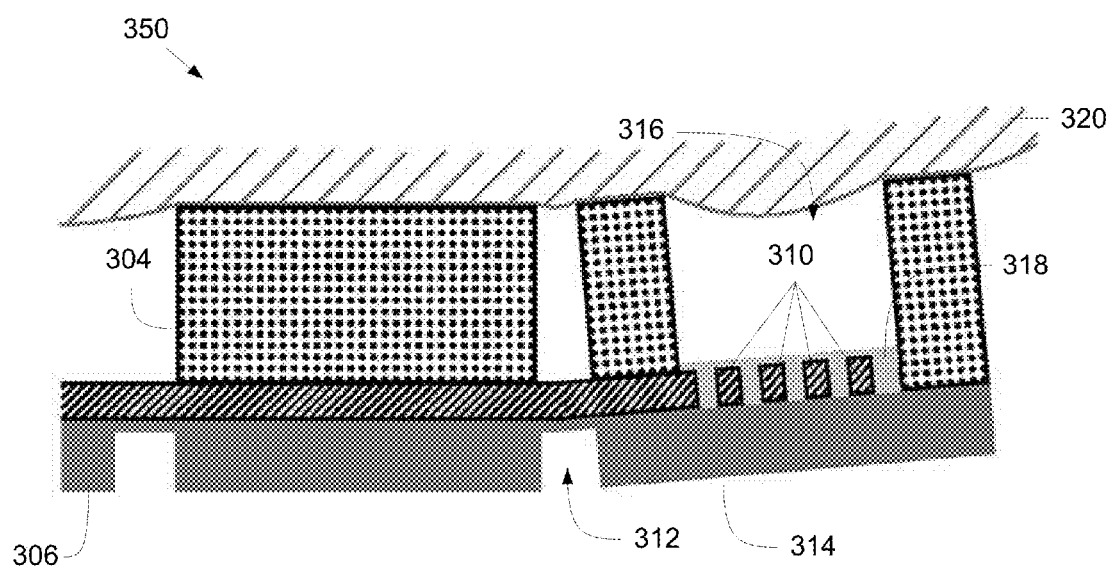
FIG. 4 is a the flexible substrate structure of FIG. 3 in a flexed position.

Referring to FIG. 4, the frame-flex coplanar waveguide structure 350 is shown in a flexed position in accommodation of a target sampling surface 320.

FIG. 4 depicts flexion across the flexible trench region 312. The rigid island region 314 remains substantially undeformed. In this example, the sensor 310 and its input connections are bent along with the substrate 306 to conform to the target sample surface 320, which may be a biological tissue such as human skin or other animal or plant tissue.

According to some embodiments, the sensor 310 may consist of a thick-metal inter-digital capacitor thinly covered by a selected chemi-absorbent polymer 318. Due to the rigidity of the island regions 314, the sensor 310 may not suffer substantial mechanical deformation upon bending, and the original physical dimensions and related electrical properties of the sensor 310 may be preserved.

According to some embodiments, the pocket 316 formed by the polymeric frame members 322 constructed from the structural frame layer 304 generally prevents the chemi-absorbent polymer 318 from overflowing out of the desired area. Furthermore, the depth of the pocket 316 assists in inhibiting contact of the sensor 310 by the target sample surface 320, which may otherwise disrupt or damage the sensor 310.

A chemi-absorbent polymer layer 318 may be deposited at the bottom of pocket 316 and on top of the capacitor portion of the sensor 310. A chemi-absorbent polymer is a polymer for which the material properties of the polymer vary in the presence of a particular chemical or chemicals. These particular chemicals may also be referred to as analytes.

For example, the dielectric properties, permittivity, electrical susceptibility, etc. of some chemi-absorbent polymers may change in the presence of a particular analyte or analytes, such that the capacitance of an electrical structure that includes a chemi-absorbent polymer may change in the presence of the analyte or analytes.

For example, the pocket 316 may be loaded with any chemi-absorbent polymer or other analyte-reactive substance. Numerous examples of commercially-available chemi-absorbent polymers can be found, in respect of such analytes as ethanol (EtOH), methanol (MeOH), methane ($CH_4$), acetone etc.

The frame-flex coplanar waveguide structure 350 may be used as an epidermal ethanol resonant sensor. According to other embodiments, various analytes may be detected from a target sample by loading the pocket 316 with other chemi-absorbent polymers, or other analyte-reactive substances.

According to some embodiments, more than one type of chemi-absorbent polymer or analyte-reactive substance may be used within a single sensor array, in order to detect more than one analyte or ambient condition.

According to some embodiments, multiple sensors or arrays may be arranged in cascade, and each may include the same chemi-absorbent polymer. In such a case, the cascade arrangement and use of a single chemi-absorbent polymer (corresponding to a specific analyte) may provide greater sensitivity to the analyte as compared to a single sensor or array.

According to other embodiments, multiple sensors within an array, or multiple arrays arranged in cascade may include multiple chemi-absorbent polymers. This may allow for a sensor array or cascade of arrays to be sensitive to more than one analyte. This may provide for the detection and analysis of chemical interference, for example, within the vapors collected from a particular tissue.

For example, a target analyte, such as ethanol, may be of particular interest. However, the target analyte may exist in the presence of interfering compounds, such as methanol or methane. In such a case, it may be interesting to know not only that ethanol is contained in the vapor collected from a tissue sample, but to also know that methanol and/or methane are present as well.

In some cases, the use of multiple chemi-absorbent polymers in a sensor array or cascade of arrays may allow for the mere detection of both a target analyte and interfering compounds. In other cases, the use of multiple-chemi-absorbent polymers in a sensor array or cascade of arrays may allow for individual concentrations of the target analyte and interfering compounds to be detected.

According to some embodiments, the pocket 316 of a particular frame-flex coplanar waveguide structure 350 may contain a zero-reactive substance, for example, which may not be reactive to a particular target analyte or interfering compound. A sensor with a zero-reactive substance may be used in order to determine a base-line measurement, which may be used in correlation with measurements taken from sensors containing a chemi-absorbent polymer.

In some cases, a selection of multiple chemi-absorbent polymers can be made in order to detect multiple analytes that are indicative of bodily health in general. For example, acetone levels may provide an indication of diabetes or the imminent onset of diabetes attack; TCP may be an indication of marijuana use; and certain cancerous conditions may be correlated with the presence of particular gaseous biomarkers.

According to some embodiments, there may be around thirty or more different target analytes and/or interfering compounds that may be detected by a sensor array or cascade of sensor arrays.

In some implementations, a single-port, two-resonator sensor array may be constructed on a substrate 306 that includes Kapton® polymide flexible substrate. A 100-μm layer of polymer SU-8 may be used as the structural frame layer 304.

Figure 5A:
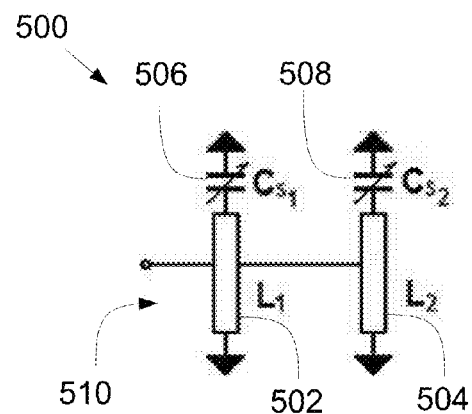
FIG. 5a is a circuit diagram of a single-port, multi-inductor-capacitor resonant sensor array, according to some embodiments.

FIG. 5a shows an example single-port, two-resonator sensor array 500 consisting of a first inductor 502, a second inductor 504, a first capacitor 506, and a second capacitor 508, with an associated port 510.

Figure 5B:
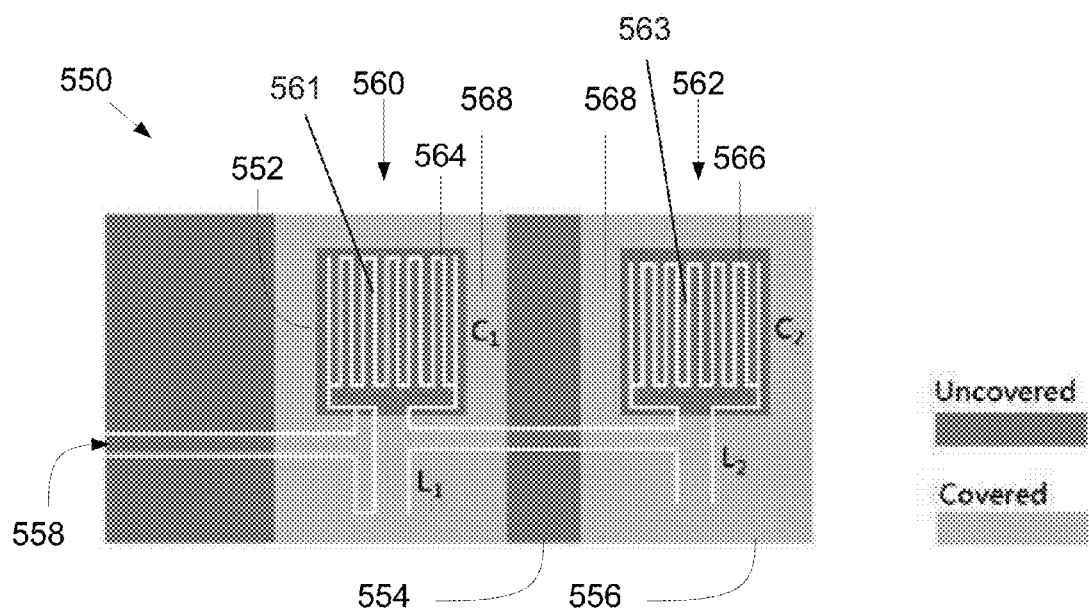
FIG. 5b is a plan view of a single-port, multi-resonator sensor array in a coplanar waveguide implementation, according to some embodiments.

A single-port, two-resonator sensor array may be implemented using a coplanar waveguide configuration. An example of a coplanar waveguide single-port, two-resonator sensor array 550 is shown in FIG. 5b. In this implementation, the coplanar waveguide sensor array 550 includes a trace 552 or a conductive layer such as copper or gold, placed on a substrate.

Some regions 554 of the substrate may be uncovered, while other regions 556 of the substrate may be covered, as indicated by darker and lighter shading, respectively, in FIG. 5b. For example, the single-port, two-resonator sensor array may be constructed on a rigid-flex substrate, that includes a substrate layer such as a Kapton® polyimide layer, and a conductive layer such as gold or copper. The rigid-flex substrate may be covered, in particular regions, by a structural frame layer. According to some embodiments, the structural frame layer comprise an SU-8 polymeric coating. According to some embodiments, this layer may be of a thickness of around 100 μm. In other embodiments, the thickness of the structural frame layer may be less or more than 100 μm (e.g. 50 μm to several millimeters) depending, for example, on the amount of separation required between the sensor and the sample surface.

In some embodiments, the structural frame layer may comprise polymer materials and/or non-polymer materials such as metal, metal oxides, ceramics, or other structural materials.

The particular geometry of the trace 552 may result in electrical characteristics that can be modeled as a first capacitance (e.g. $C_1$), a second capacitance (e.g. $C_2$), a first inductance (e.g. $L_1$), and a second inductance (e.g. $L_2$) as seen by a port 558.

The particular geometry of the trace 552, in other words, the electrical characteristics, may determine the resonance characteristics of a first sensor block 560 and a second sensor block 562, having sensors 561 and 563 respectively, each having capacitor portions 564 and 566.

According to some embodiments, the structural frame layer covering the rigid-flex layer may form frame members 568 surrounding capacitor portions 564 and 566. Capacitor portions 564 and 566 may remain uncovered, corresponding to pockets surrounded by the frame members 568. According to some embodiments, the pockets may be polymer pockets, which may be loaded with chemi-absorbent polymers as previously described.

According to some applications, the responses of a resonant sensor can be obtained either by transmission response (e.g. scattering parameter $S_{12}$) or reflection response (e.g. scattering parameter $S_{11}$). In both cases, the sensor is excited with electrical signals of different frequencies, and a reading is measured as the ratio between the supplied power and the returned power. In this case, the supplied power serves as a reference. When a resonant sensor is sensitive to ambient parameters, such as analytes from a target sampling surface, the returned power may vary with the sensor response against the ambient parameter or analyte.

The ratio between the supplied power and the returned power may consist of simple amplitude representations of the sensor readout, or the complex amplitude-phase representation from which multiple readout parameters can be derived.

Figure 6:
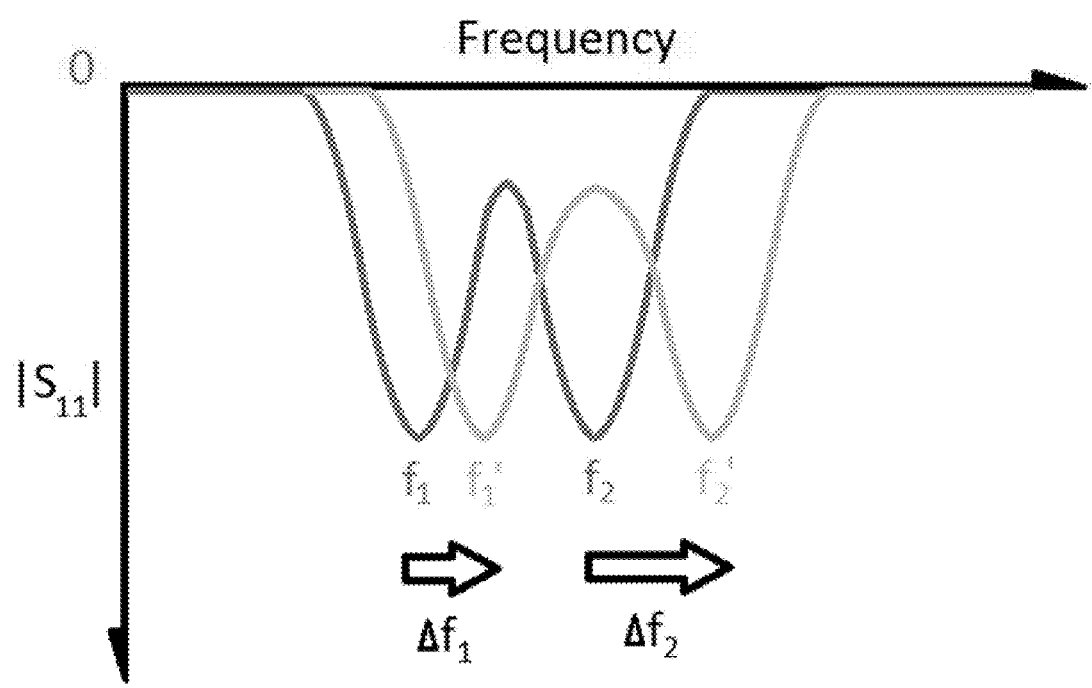
FIG. 6 is a reflection response curve of a single-port, multi-resonator sensor array as taken at the array input.

The reflection response curve, showing scattering parameter $S_{11}$ of a sing-port, multi-resonator sensor array is shown in FIG. 6. Based on the properties of the individual resonating elements of the single-port, two-resonator sensor arrays, and their responsiveness against changes in ambient parameters due to the chemi-absorbent polymers, the resonant frequencies of the sensor 561 and sensor 563 will shift accordingly.

Referring to FIG. 6, an initial resonant frequency $f_1$ of a first sensor in a sensor array, and an initial resonant frequency $f_2$ of a second sensor in a sensor array are shown. In the presence of an analyte, the resonant frequency of each sensor shifts to a new resonant frequency, $f_1'$ and $f_2'$ respectively, due to a change in capacitance and/or inductance as determined by a chemi-absorbent polymer used in the sensor structure. The frequency shift can be depicted accordingly, where $\Delta f_1 = f_1' - f_1$ and $\Delta f_2 = f_2' - f_2$.

According to some embodiments, two sensors in a sensor array may share the same electrical connection from the input port. In this case, an inter-resonator interference (also known as a resonator coupling) may cause the two sensors to interfere with each other. In other words, a change in the resonant frequency of one sensor may cause a proportional shift in the resonant frequency of the other. A coupling effect may introduce significant inaccuracy in a sensor's readout.

In order to effectively decouple the sensor readings and obtain readout values free of inter-sensor interference, a coupling matrix model may be used. The coupling matrix model may be obtained from the general form of a two-port coupling matrix circuit model and its respective mathematic representation, and then modifying this to a single-port, multi-resonator model by terminating one port of the two-port model with an open-circuit load in order to model the two-resonator sensor array.

Figure 7:
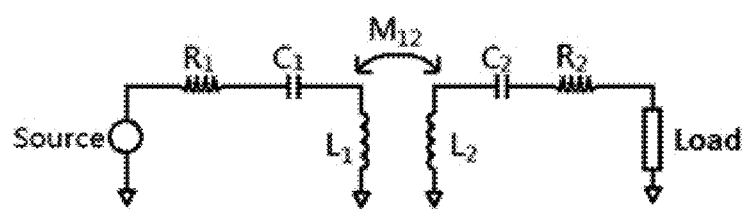
FIG. 7 is a circuit diagram showing a coupling matrix model for a multi-resonator structure and the single-port modified model for the resonant sensor array readout.
Figure 7:
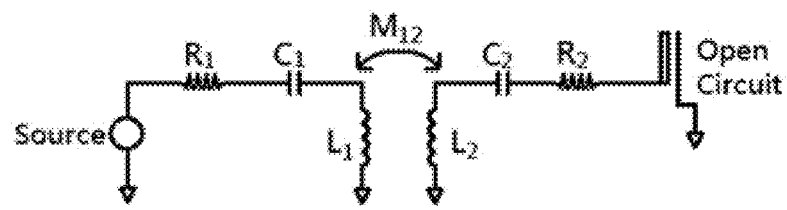

FIG. 7 depicts the general form of a two-port coupling matrix circuit model 700 and a single-port, multi-resonator model with an open-circuit load 750. Each circuit is composed of circuit elements including resistors $R_1$ and $R_2$, capacitors $C_1$ and $C_2$, and inductors $L_1$ and $L_2$. $M_{12}$ represents the coupling between the first resonator and the second resonator.

In view of the general form of a two-port coupling matrix model 700, scattering parameters $S_{11}$ and $S_{12}$ (reflection and transmission parameters respectively) can be given in the form:

$$S_{11} = 1 + 2jR_S[\lambda I - jR + M]_{11}^{-1}, \text{ and}$$

$$S_{12} = -2j\sqrt{R_S R_L}[\lambda I - jR + M]_{21}^{-1}, \text{ where:}$$

M is a coupling matrix containing the values of mutual couplings between the nodes of the network;
I is the identify matrix;

$$\lambda = \frac{f_0}{BW}\left(\frac{f}{f_0} - \frac{f_0}{f}\right);$$

$f_0$ is the center frequency;
R is a termination impedance matrix; and
$R_s$ and $R_L$ are values modeling a source and load resistance respectively.

The termination impedance matrix R is composed such that it contains the values of the source impedance (e.g. $R_s$) in the lowest-ordered row, lowest-ordered column corner element (e.g. top left corner), and the load impedance (e.g. $R_L$) in the element of the highest-ordered column, highest-ordered row (e.g. bottom right corner) of the matrix. (All other elements are generally zero).

The coupling matrix M can be composed containing the values of mutual couplings between the nodes of a network. For example, the matrix element $M_{12}$ can represent the coupling between the first resonator and the second resonator. The matrix element $M_{11}$ can represent the mutual coupling of the first resonator.

The coupling matrix M can be written in the form:

$$M = \begin{bmatrix} M_{11} + \Delta M_{11} & M_{12} \\ M_{21} & M_{22} + \Delta M_{22} \end{bmatrix},$$

where $\Delta M_{11}$ and $\Delta M_{22}$ represent a change to the self-couplings $M_{11}$ and $M_{22}$ respectively.

For example, in a single-port, two-resonator sensor array that includes a chemi-absorbent polymer, the change in self-coupling $M_{11}$ may correspond to a change in the resonant or center frequency, e.g. $\Delta f_1$, of the first sensor as the first sensor responds to an ambient parameter or analyte corresponding to the chemi-absorbent polymer. For example, this change in resonant or center frequency may take the form of that shown in FIG. 6.

Similarly, the change in self-coupling $M_{22}$ may correspond to a change in the resonant frequency, e.g. $\Delta f_2$, of the second sensor as the first sensor responds to an ambient parameter. Each sensor may respond to a different ambient parameter, or analyte, for example, if a different chemi-absorbent polymer or analyte-reactive substance is used for each sensor.

In general, for the self-coupling of the $n^{th}$ resonator in a resonator array, the change in self-coupling, $\Delta M_{nn}$ can be expressed in terms of a frequency shift, as:

$$\Delta M_{nn} = -\frac{f_{n0}}{BW}\left(\frac{f_{n0} + \Delta f_{n0}}{f_{n0}} - \frac{f_{n0}}{f_{n0} + \Delta f_{n0}}\right),$$

where:

$f_{no}$ is the initial or modeled center frequency of the $n^{th}$ resonator (e.g. corresponding to a first ambient condition such as an absence of an analyte);
$\Delta f_{n0}$ is the change from the initial or modeled center frequency of the $n^{th}$ resonator (e.g. as measured during a second ambient condition such as the presence of an analyte); and,
BW is the bandwidth of the pass-band of the resonator.

Referring now to the single-port two-resonator model 750 of FIG. 7, the reflection, or scattering parameter $S_{11}$ can be expressed as:

$$S_{11} = 1 + 2jKR_s\left[(\lambda - jR_L + \Delta M_{22}) - \frac{M_c^2}{\lambda - jR_s + \Delta M_{11}}\right],$$

where $$K = \det([\lambda I - jR + M]) = \frac{1}{(\lambda - jR_s + \Delta M_{11})(\lambda - jR_L + \Delta M_{22}) - M_c^2}$$

It is also possible to obtain a partial derivative of $S_{11}$ against any selected self-coupling parameters or the inter-resonator coupling parameters. With this partial derivative expression, the parameters that affect the sensitivity of the selected sensor can be obtained. Furthermore, this expression can be optimized in order to maximize the sensitivity. The new expression can then be used as a reference to synthesize the new hardware implementation of the sensor array with the desired improvement to sensitivity.

For example, the above expression for $S_{11}$, using a single-port, two-resonator network in a general form can be shown as:

$$\Gamma = S_{11} = f(M_{11}, M_{22}, M_C, R_L, R_S)$$

In order to maximize the sensitivity of the first sensor in the array, the partial derivative of $S_{11}$ versus $M_{11}$ is taken, which gives:

$$\frac{\delta S_{11}}{\delta M_{11}} = f'(M_{11}, M_{22}, M_C, R_L, R_S)$$

Then, by performing an optimization procedure, the response magnitude, $S_{11}$, resulted from the change in sensor resonance behavior, $M_{11}$, can be maximized. This can be expressed as:

$$\frac{\delta S_{11}}{\delta M_{11}}(\text{Maximized}) = f'(M'_{11}, M'_{22}, M'_C, R'_L, R'_S)$$

Figure 8A:
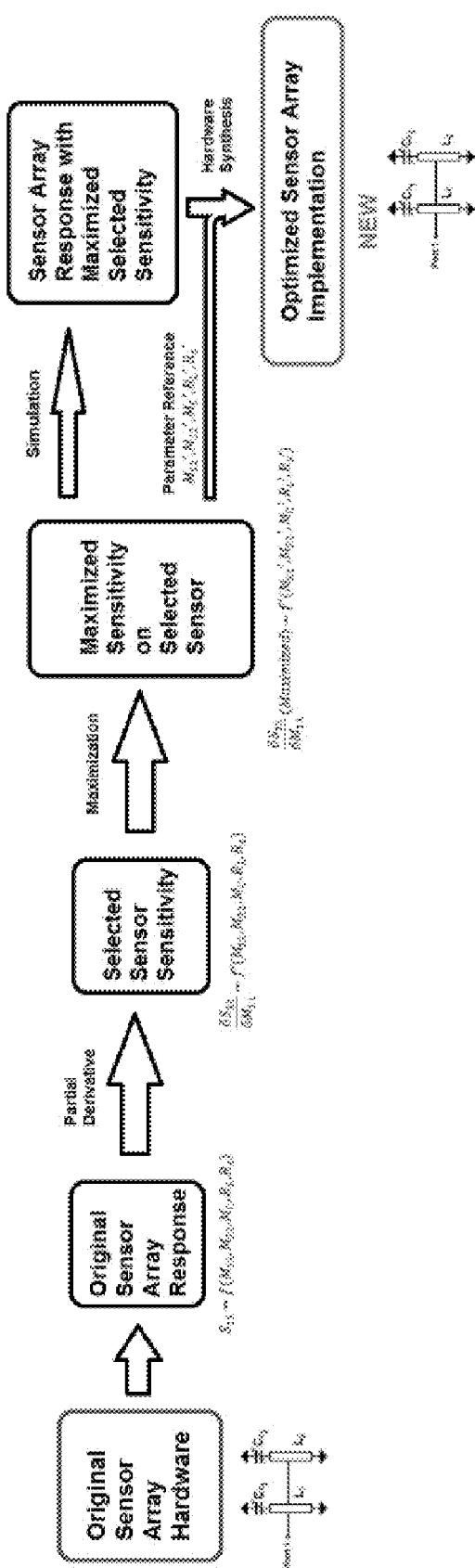
FIG. 8a is a block diagram of a sensor sensitivity optimization process.

This new set of parameters ($M_{11}'$, $M_{22}'$, $M_c'$, $R_L'$, and $R_s'$) can be applied to the original $S_{11}$ expression, and the hardware design can be changed accordingly in order to deliver the new optimized performance and sensitivity level. A sensitivity optimization process such as this is depicted in FIG. 8a.

Figure 8B:
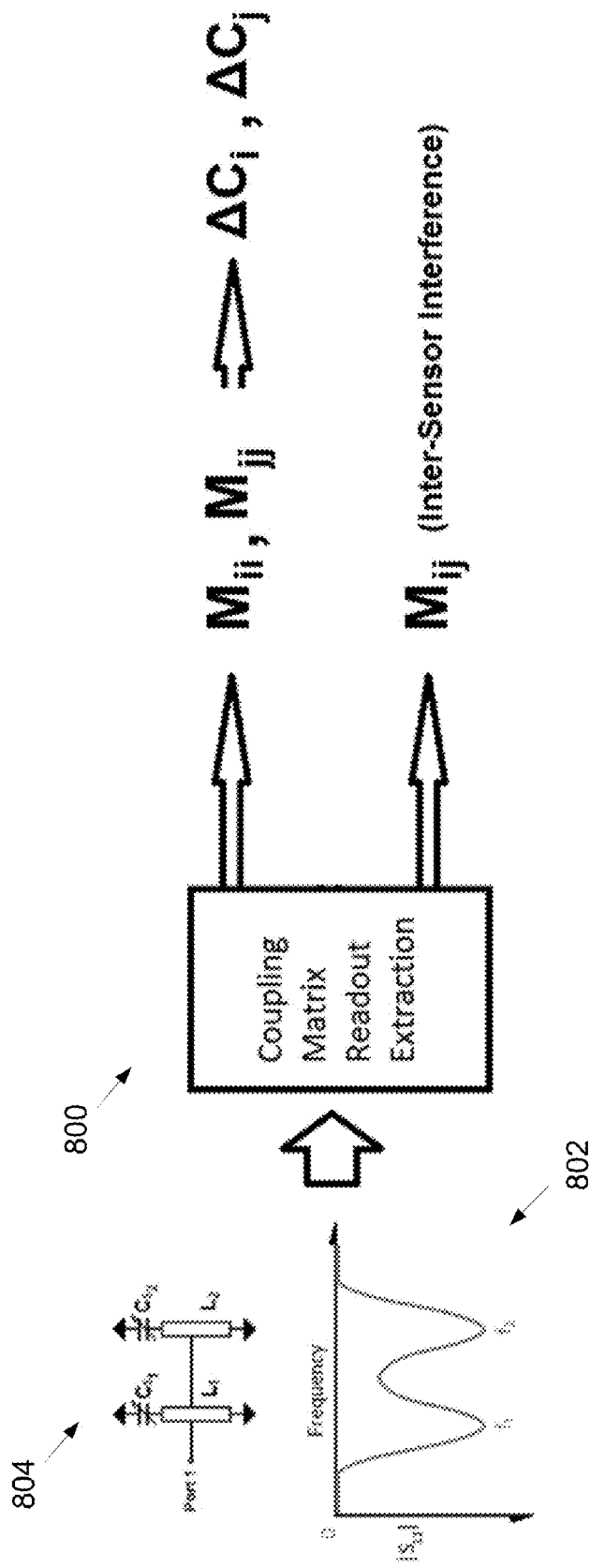
FIG. 8b is a block diagram of the parameter extraction process through a coupling matrix technique on a reflection response curve, according to some embodiments.

Referring to FIG. 8b, the expressions as described above can be used in a coupled-matrix readout extraction method. For example, an embedded readout system 800 can be used to perform model-mapping calculations on a measured response curve 802, and referring to a model 804. Using the expressions relating reflection ($S_{11}$) and self-coupling ($M_{ii}$) as described above, the relative change in capacitance and/or the relative change in inductance can be directly extracted. Using $M_{ij}$, the inter-resonator coupling (a.k.a. "inter-sensor interference") can be quantized. The parameters with absolute magnitude (e.g. capacitance, inductance, and resistance) can be derived under proper assumptions or calibrations.

Whereas absolute values may otherwise be obtained with proper baseline assumptions that can potentially deviate from the actual values, according to some embodiments, the relative change in the values for capacitance and/or inductance may be captured using the coupling matrix model analyses with very high accuracy.

According to some embodiments, the extracted parameters can be compared to parameters extracted under different ambient conditions in order to determine the presence or concentration of particular ambient conditions, such as an analyte. For example, a set of baseline parameter values may be established, through measurement or modeling, or through other known data. Similarly, parameter values may be established for known concentrations of particular analytes or other ambient conditions.

When the resonant parameters have been extracted, for example, as from the measured response curve 802, the measured resonant parameters can be compared to previously known values in order to determine a correlative factor, such as the concentration of an analyte.

Figure 9:
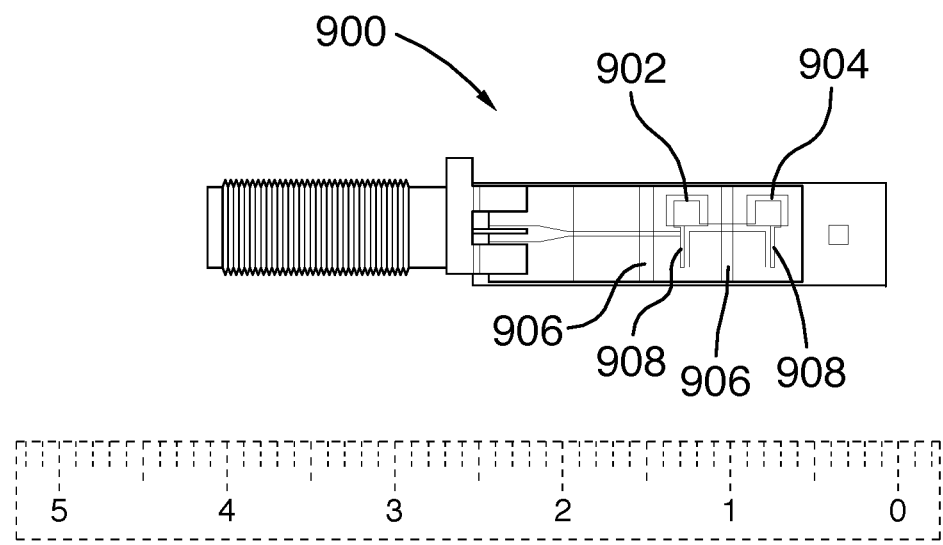
FIG. 9 is an image of a prototype single-port, two-sensor array according to one embodiment.

Referring to FIG. 9, there is shown an example two-resonator sensor array 900, comprising a first sensor 902 and a second sensor 904. Trench regions 906 can be seen, which provide flexible nodes. A structural frame layer can be seen covering rigid islands 908, which prevent physical deformation of the sensors 902 and 904 upon flexion. The pockets of sensors 902 and 904, which correspond to regions not covered by the structural frame, can also be seen.

Figure 10:
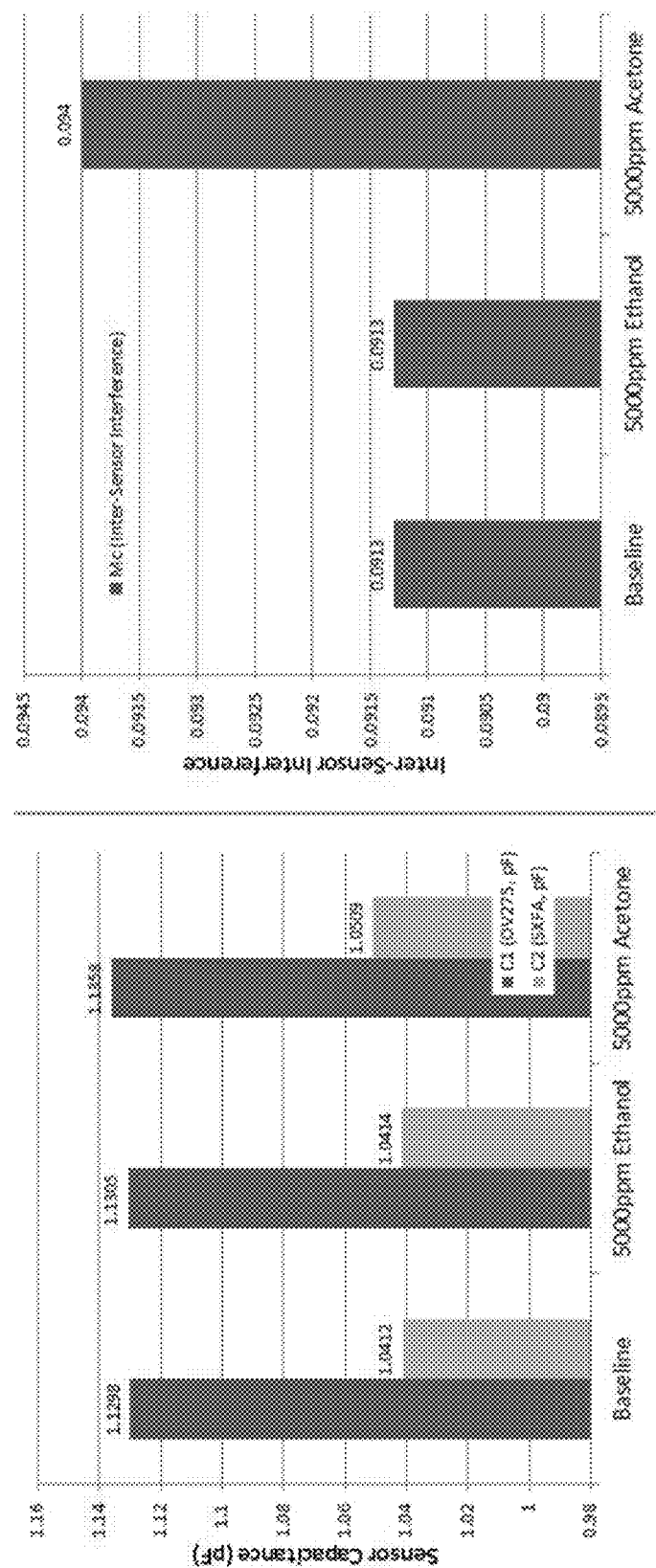
FIG. 10 is a graphical data summary taken from an exemplary sensor array readout; and, FIG. 11 is a measured response curve and a coupling-matrix model-mapped curve of an example two-resonator resonant sensor array.

The example two-resonator sensor array 900 can be used to demonstrate operability in a laboratory. An example of some resonant parameters, and in particular, sensor capacitance (e.g. $C_1$ and/or $C_2$ as in FIG. 8), and inter-sensor interference ($M_c$) are shown in FIG. 10, based on the laboratory demonstration of the sensor array 900. In the laboratory demonstration, sensors 902 and 904 are loaded with commercially-available polymers OV-275 and SXFA for gaseous analyte detection.

In the example, the sensor array 900 is exposed to 5,000 ppm of gaseous ethanol and acetone vapor, and the respective reflected sensor array response curves are obtained. The single-port multi-sensor coupling matrix analysis technique is then employed. A single-port, two-resonator coupling matrix model is also applied, in order to generate estimated sensor array response curves.

Referring to FIG. 10, a measured frequency-response curve for the reflection $S_{11}$ is shown along with a model-mapped response, in relation to the example sensor array 900 exposed to 5,000 ppm of gaseous ethanol and acetone vapor. Capacitances of both sensors 902 and 904, as well as the interference factors derived from the curve is shown in FIG. 11.

Figure 11:
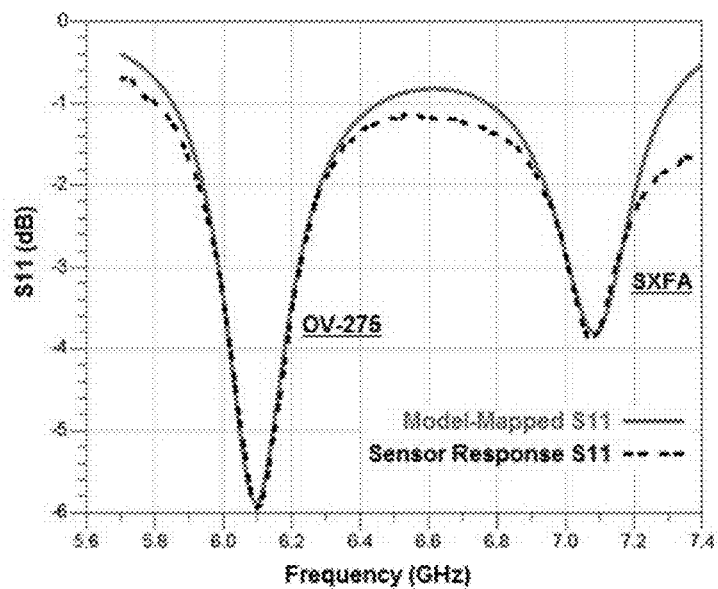
Figure 11:
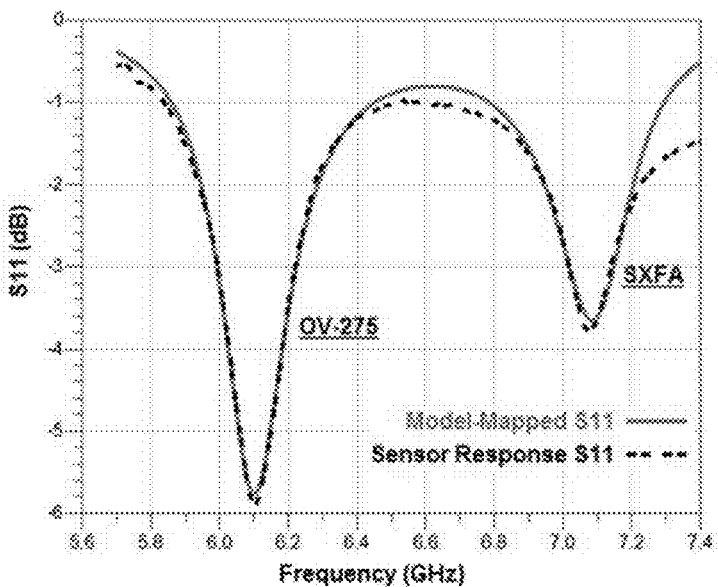

Referring to FIG. 11, changes in sensor capacitance and inter-sensor interference as related to the measured $S_{11}$ curve of FIG. 10 are shown. The example shown demonstrates the change in sensor capacitance and inter-sensor interference as measured for a known concentration of the analytes ethanol and acetone.

According to some embodiments, if a concentration of analytes, such as ethanol and acetone, are not known at the time that the sensor capacitance and inter-sensor interference are measured, the measured values can be compared with previously known values, such as the estimated sensor array response curves that have been previously generated. The comparison of the measured values and the previously-known or generated values can be used to determine the concentration of the ambient analytes.

While the above description provides examples of one or more apparatus, methods, or systems, it will be appreciated that other apparatus, methods, or systems may be within the scope of the claims as interpreted by one of skill in the art.

The invention claimed is:

1. An apparatus for sensing an analyte, comprising:
   a substrate having a first rigid region and a first trench region, the first trench region being thinner than the first rigid region; and
   a sensor block supported by the first rigid region, the sensor block comprising:
      a frame layer extending upwardly from the first rigid region, the frame layer having a first end opposite the substrate to engage with a tissue sample, the frame layer having an opening therein extending between the substrate and the first end defining a pocket; and
      a sensor located within the pocket distal the first end, the sensor comprising:
         a first substance having a property adapted to change in response to the presence of the analyte; and
         a resonant element covered by the first substance and operable to detect the change in the property of the first substance;
   wherein the first trench region is laterally positioned relative to the first rigid region and the sensor block to provide for flexed deformation of the substrate within the first trench region upon flexing the substrate.

2. The apparatus of claim 1, wherein the substrate has a second rigid region coupled to the first rigid region, and further comprising a second sensor block supported by the second rigid region.

3. The apparatus of claim 2, wherein the second rigid region is coupled to the first rigid region via the first trench region.

4. The apparatus of claim 3, further comprising a second trench region laterally positioned relative to the second rigid region to provide for flexed deformation of the substrate within the second trench region upon flexing the substrate.

5. The apparatus of claim 3, wherein the substrate comprises a polyimide layer underneath a conductive layer.

6. The apparatus of claim 1, wherein the first substance is a chemi-absorbent polymer.

7. The apparatus of claim 6, wherein the property of the chemi-absorbent polymer changes in response to the presence of ethanol.

8. The apparatus of claim 1, wherein a cross-section of the first trench region has a rectangular shape.

9. The apparatus of claim 1, wherein the sensor is implemented by a coplanar waveguide structure.

10. The apparatus of claim 9, wherein a section of the coplanar waveguide structure corresponding to a capacitance section is exposed within the pocket.

* * * * *